United States Patent
Mercuri

(10) Patent No.: US 12,036,235 B2
(45) Date of Patent: Jul. 16, 2024

(54) COMPOSITION IN SOLID FORM FOR USE IN THE TREATMENT OF EXTRAOESOPHAGEAL SYMPTOMS OF GASTRIC REFLUX

(71) Applicant: DRUGS MINERALS AND GENERICS ITALIA S.R.L. IN FORMA ABBREVIATA D.M.G. ITALIA S.R.L., Pomezia RM (IT)

(72) Inventor: Luigi Mercuri, Pomezia RM (IT)

(73) Assignee: DRUGS MINERALS AND GENERICS ITALIA S.R.L. IN FORMA ABBREVIATA D.M.G. ITALIA S.R.L., Pomezia RM (IT)

( * ) Notice: Subject to any disclaimer, the term of this patent is extended or adjusted under 35 U.S.C. 154(b) by 472 days.

(21) Appl. No.: 16/966,402

(22) PCT Filed: Feb. 13, 2019

(86) PCT No.: PCT/IB2019/051158
§ 371 (c)(1),
(2) Date: Jul. 30, 2020

(87) PCT Pub. No.: WO2019/159073
PCT Pub. Date: Aug. 22, 2019

(65) Prior Publication Data
US 2020/0360421 A1 Nov. 19, 2020

(30) Foreign Application Priority Data
Feb. 13, 2018 (IT) .................. 102018000002625

(51) Int. Cl.
| | | |
|---|---|---|
| *A61K 31/734* | (2006.01) | |
| *A61K 9/00* | (2006.01) | |
| *A61K 31/80* | (2006.01) | |
| *A61K 33/10* | (2006.01) | |
| *A61K 9/14* | (2006.01) | |
| *A61K 9/20* | (2006.01) | |
| *A61K 9/48* | (2006.01) | |

(52) U.S. Cl.
CPC ............ *A61K 31/734* (2013.01); *A61K 31/80* (2013.01); *A61K 33/10* (2013.01); *A61K 9/0053* (2013.01); *A61K 9/14* (2013.01); *A61K 9/20* (2013.01); *A61K 9/48* (2013.01)

(58) Field of Classification Search
CPC ...... A61K 9/205; A61K 47/36; A61K 9/1652; A61K 33/10; A61K 31/734; A61K 31/80; A61K 47/44; A61K 9/20; A61K 9/14; A61K 9/0053; A61K 9/48
USPC ...................................................... 514/54
See application file for complete search history.

(56) References Cited

U.S. PATENT DOCUMENTS

| | | | | |
|---|---|---|---|---|
| 5,646,130 | A * | 7/1997 | Shi ............. | C08B 37/0084 536/123 |
| 5,776,494 | A * | 7/1998 | Guskey ......... | A61K 47/183 424/DIG. 5 |
| 2005/0069583 | A1* | 3/2005 | Axford ......... | A61P 1/04 424/464 |
| 2016/0243144 | A1* | 8/2016 | Garegnani ...... | A61K 31/437 |

FOREIGN PATENT DOCUMENTS

| | | | | |
|---|---|---|---|---|
| EP | 1468677 | A2 | 10/2004 | |
| EP | 1676585 | A1 * | 7/2006 | ........... A61K 31/734 |
| EP | 3124048 | A1 | 2/2017 | |
| WO | WO 94/12180 | A1 | 6/1994 | |
| WO | WO 95/01795 | A1 | 1/1995 | |
| WO | WO 95/11667 | A1 | 5/1995 | |
| WO | WO 2010/038241 | A2 | 4/2010 | |
| WO | WO-2014113269 | A1 * | 7/2014 | |
| WO | WO-2017013542 | A1 * | 1/2017 | ........... A61K 31/295 |

OTHER PUBLICATIONS

Smart et al. (Journal of the Royal Society of Medicine, vol. 83 Sep. 1990, 554-556).*
Tsoukali et al. (Annals of Gastroenterology (2013) 26, 1-6).*
O'Lenick (Cosmetics & Toiletries; Mar. 10, 2010).*
KCC Basildon, Simethicone Antifoam C100F, product page, Aug. 2017. (Year: 2017).*
Product page for DC-193, downloaded from the internet Apr. 17, 2023. (Year: 2023).*
Rottholtz. Regarding the non-gastrointestinal aspects of reflux, 2015, internet article, https://www.rothholtzmd.com/wp-content/uploads/2015/01/non-gastrointestinal-aspects-of-reflux.pdf. (Year: 2015).*
Balestrazzi et al., "A new therapeutic approach for the Dry Eye Syndrome in patients with laryngopharyngeal reflux: first data", Acta Biomed, 2020, vol. 91, Supplement 1: 36-42.
Bonini et al., "Association of Dry Eye with Laryngopharyngeal Reflux in Clinical Practice", Current Eye Research, 2021, DOI: 10.1080/02713683.2021.1971721.
Bonini et al., "Inflammation and Dry Eye-like Symptoms as Concomitant Manifestations of Laryngo-Pharyngeal Reflux", 2023, Current Eye Research, DOI: 10.1080/02713683.2023.2207210.

(Continued)

*Primary Examiner* — Layla D Berry
(74) *Attorney, Agent, or Firm* — James S. Keddie; Bozicevic, Field & Francis LLP

(57) ABSTRACT

The present invention regards a mixture in solid form comprising or, alternatively, consisting of (a) alginic acid, or a salt thereof, (b) a bicarbonate and/or carbonate salt and (c) a simethicone and/or dimethicone, for use in a treatment, in particular in a curative and/or preventive treatment, of extraoesophageal disorders or symptoms caused or triggered by gastroesophageal reflux disease (GERD) or by a partial backflow of the gastric content, such as for example by the partial backflow of pepsin, hydrochloric acid, gastric juices or acid gastric vapours, from the stomach and which occur, said disorders or symptoms, in an extraoesophageal area.

13 Claims, No Drawings

(56) References Cited

OTHER PUBLICATIONS

Di Zazzo et al., "Ocular Surface Disease as Extraesophageal Gastroesophageal Reflux Disease Manifestation: A Specific Therapeutic Strategy", Cornea, 2023, vol. 00, No. 00, 6 pages.
Iannella et al., "Investigation of pepsin in tears of children with laryngopharyngeal reflux disease", International Journal of Pediatric Otorhinolaryngology, 2015, 79: 2312-2315.
Magliulo et al., "Laryngopharyngeal Reflux Disease in Adult Patients: Tears and Pepsin", Journal of Biological Regulators & Homeostatic Agents, 2020, 34(2): 715-720.
Mazzacane et al., "Eye reflux: an ocular extraesophageal manifestation of gastric reflux", Int. J. Ophthalmol, 2018, 11(9): 1503-1507.
Messmer, "Pathophysiology of dry eye disease and novel therapeutic targets", Experimental Eye Research, 2022, 217: 108944, 8 pages.
Plateroti et al., "Evidence of Pepsin-Related Ocular Surface Damage and Dry Eye (PROD Syndrome) in Patients with Laryngopharyngeal Reflux", Life, 2020, 10: 202, 8 pages.
Bardhan et al., "Reflux Revisited: Advancing the Role of Pepsin", Hindawi Publishing Corporation, International Journal of Otolaryngology, 2012, Article ID 646901, 13 pages.
Ciprandi et al., "A combined treatment for patients with dry eye and associated laryngopharyngeal reflux: a real-life approach", Int J Ophthalmol, Oct. 18, 2023, 16(10): 21-27.
Drobnic et al., "Efficacy of artichoke and ginger extracts with simethicone to treat gastrointestinal symptoms in endurance athletes: a pilot study", Minerva Gastroenterology, Mar. 2022, 68(1): 77-84.
Holtmann et al., "A randomized placebo-controlled trial of simethicone and cisapride for the treatment of patients with functional dyspepsia", Aliment Pharmacol Ther, 2002, 16: 1641-1648.
Kim et al., "Effects of pepsin and pepstatin on reflux tonsil hypertrophy in vitro", PLOS One, Nov. 2018, 13(11): e0207090, 12 pages.
Lechien, "Treating and Managing Laryngopharyngeal Reflux Disease in the Over 65s: Evidence to Date", Clinical Interventions in Aging, Nov. 2022, 17: 1625-1633.
Miraglia Del Giudice et al., "Magnesium Alginate in Children With Uncontrolled Asthma", Journal of Biological Regulators & Homeostatic Agents, 2019, 0393-974X, pp. 37-43.
U.S. Food and Drug Administration, "Over-the-Counter (OTC) Monograph M002: Antiflatulent Products for Over-the-Counter Human Use", Sep. 20, 2021, 3 pages.
Pizzorni et al., "Magnesium alginate versus proton pump inhibitors for the treatment of laryngopharyngeal reflux: a non-inferiority randomized controlled trial", European Archives of Oto-Rhino-Laryngology, Jan. 15, 2022, https://doi.org/10.1007/s00405-021-07219-0, 10 pages.
Salvatore et al., "The Effect of Alginate in Gastroesophageal Reflux in Infants", Pediatric Drugs, Sep. 4, 2018, https://doi.org/10.1007/s40272-018-0314-0, 9 pages.
Samuels et al. "Pepsin in gastroesophageal and extraesophageal reflux: molecular pathophysiology and diagnostic utility", Curr Opin Otolaryngol Head Neck Surg, Dec. 2020, 28(6): 401-409.
Ummarino et al., "Effect of Magnesium Alginate Plus Simethicone on Gastroesophageal Reflux in Infants", JPGN, 2015, 60(2): 230-235.

\* cited by examiner

COMPOSITION IN SOLID FORM FOR USE IN THE TREATMENT OF EXTRAOESOPHAGEAL SYMPTOMS OF GASTRIC REFLUX

CROSS-REFERENCE TO RELATED APPLICATIONS

This application is a § 371 national phase of International Application No. PCT/IB2019/051158, filed on Feb. 13, 2019, which claims the benefit of Italian Application No. 102018000002625, filed on Feb. 13, 2018, which applications are incorporated by reference herein.

The present invention regards a mixture in solid form comprising or, alternatively, consisting of (a) alginic acid, or a salt thereof, (b) a bicarbonate and/or carbonate salt and (c) a simethicone and/or dimethicone, for use in a treatment, in particular in a curative and/or preventive treatment, of extraoesophageal disorders or symptoms caused or triggered by gastroesophageal reflux disease (GERD) or by a partial backflow of the gastric content, such as for example by the partial backflow of pepsin, hydrochloric acid, gastric juices or acid gastric vapours, from the stomach and which occur, said disorders or symptoms, in an extraoesophageal area.

In the context of the present invention, the expression "composition" is used to indicate a pharmaceutical composition or a medical device composition or a supplement composition or a food composition (the composition/s of the present invention for the sake of brevity).

In otorhinolaryngology, the expression "extraoesophageal reflux" is used to identify the irritative condition caused by the contact between the gastric acid (or gastric acid content) which flows back up to the level of the larynx and the upper respiratory airways in general. As a matter of fact, it is very frequent for the reflux to be observed with these symptoms (extraoesophageal reflux symptoms) only and not through the classical and widely known "heartburn" due to GERD (gastroesophageal reflux disease).

As concerns this, it would probably be more appropriate to distinguish two different nosological conditions: the classical gastroesophageal reflux (characterised by the classic retrosternal burning symptom) and extraoesophageal reflux (in which the main symptoms are for example dry cough, dysphonia, globus pharyngis). Contrary to what occurs in the classical reflux, the latter condition is characterised by irritation of the larynx caused by the reflux of gastric acids which end up affecting the upper respiratory airways. Despite the fact that the two conditions could coexist in some cases, more frequently than not this does not occur. As would be logical to expect due to the nature of the declared symptoms, patients with extraoesophageal reflux symptoms much more frequently undergo an otorhinolaryngology check-up rather than a gastroenterology check-up. Due to this reason, it is common for ORL (otorhinolaryngology) specialists to be the first to diagnose reflux in a subject unaware of suffering from this disorder up to then. Contrary to what occurs in "classical reflux", where the reflux events mainly occur at night, in case of extraoesophageal reflux it has been proven that the events occur throughout the 24 hrs.

Gastroesophageal reflux is a para-physiological condition or disease characterised by the backflow of the gastric content of the acid type which for example comprises pepsin, hydrochloric acid, gastric juices and acid gastric vapours from the stomach to the oesophagus. After deglutition, the ingested food normally passes through a canal, the oesophagus, which drives the food bolus from the mouth into the stomach; here, the highly acid environment allows the digestion of the food, which is absorbed in the intestine.

The cardia is the anatomic conjunction region between the oesophagus and the stomach, normally located in the abdomen between 2 and 4 cm below the diaphragm. Anatomically speaking, the cardia is considered part of the stomach nowadays. In the cardia there occurs the transition between the oesophageal mucosa and the gastric mucosa.

Right upstream of the cardia, the circular muscle fibres of the oesophagus acquire a sphincter action, in the sense that they remain contracted in the rest condition, while they relax during eructation, the descent of the food into the stomach and its backflow when vomiting; in the other stages of the digestive process, instead, this functional sphincter should normally remain shut and contracted, so as to prevent the acid gastric content of the stomach from flowing back into the oesophagus, irritating the inner walls thereof. The sphincter we are talking about is known as the cardiac sphincter, gastroesophageal sphincter, lower esophageal sphincter (LES) or cardia.

Cardia incapacity, more or less temporary, such to make the reverse movement of the gastric content possible, occurs in patients suffering from gastroesophageal reflux disorders or symptoms or diseases (GERD). In patients suffering from GERD, part of the gastric content flows back from the stomach to the oesophagus, which is not provided with systems for protection for example against hydrochloric acid or against gastric juices or against acid gastric vapours produced by the stomach. Gastric juice is a secretion produced by the internal mucosa of the stomach containing mucus, salts, water, digestive enzymes (such as for example pepsin) and hydrochloric acid. The pH of the gastric content or gastric juice is very low, but for example variable between 1 and 2 in any case.

Thus, in patients suffering from GERD, the backflow—even at very small amounts—of the gastric content from the stomach to the oesophagus causes the irritation of the epithelium of the oesophagus, which causes a burning feeling at the retrosternal position and pains upon deglutition, as well as an increase of caries (due to the corrosion of the teeth enamel caused by the gastric acids), retching after taking food, acidity feeling at the upper part of the oesophagus and in the pharynx (particularly frequent when one lies horizontally after eating, due to the fact that this facilitates the backflow process of the gastric content into the oesophagus). gastroesophageal reflux is very common, temporary at times, sometimes a symptom of a much more serious disease. The most common causes can be obesity, diabetes mellitus, conditions of increased gastric secretion, pregnancy, smoking, alcohol, hiatal hernia (congenital condition in which the position of the oesophagus hiatus, the opening of the oesophagus in the stomach, is in an unusual position that facilitates the backflow of the gastric content).

The pharynx is a canal that places the throat in communication with the oesophagus. Having a muscle-mucosa structure, it represents both the first tract of the digestive tube—it actually receives the food bolus from the mouth through deglutition—and a part of the upper airways: the air coming from the nose enters into the pharynx, and from the pharynx it enters into the larynx. Thus, both the food way and the airways converge into the pharynx and then proceed into the oesophagus and larynx respectively. This canal, about 15 centimetres long, starts from behind the nasal cavities, the mouth and the larynx and extends vertically from the cranial base up to the sixth cervical vertebra. The pharynx is generally divided into three tracts: the rear portion of the nasal airways (nasopharynx), the so-called throat (oropharynx) and the laryngeal part (laryngopharynx). The nasopharynx and oropharynx are separated by a specific portion of the palate: the soft palate (which represents the extension of the hard palate). The nasal cavities communicate with the pharynx by means choanae, the mouth by means of the isthmus of the fauces i.e. the narrow opening representing the transition from the oral cavity to the pharyngeal one delimited—at the upper part—by the vacant margin of the soft palate, by two pairs of folds of the mucosa at the sides and by the base of the tongue and the larynx through the laryngeal orifice. All these communications occur at the front wall of the organ, which is thus mostly incomplete. The pharynx has two main functions: i) being the first section of the digestive tube, the pharynx places the mouth in communication with the oesophagus thus allowing the food bolus to pass through by means of deglutition, and ii) being part of the upper airways, the pharynx allows air to pass through from the nasal cavities to the larynx.

Besides the disorders of the oesophagus area, patients suffering from gastroesophageal reflux may also suffer from disorders (for example indisposition or mild illness), symptoms (for example occurrence of a pathological condition or even a set of conditions through which a disease occurs) or pathologies (diseases) in extraoesophageal areas, such as the pharynx, the larynx, the oropharynx, the nasopharynx, the eye or the eye bulb and the periocular region (which is located around the eye or which regards the eye contour).

Disorders or symptoms similar to those felt in an extraoesophageal area may occur even in subjects not suffering from gastroesophageal reflux, the latter as generally defined, following the backflow for example of the acid gastric vapours from the stomach to an extraoesophageal area.

The reflux of the gastric content, such as for example the backflow of pepsin, hydrochloric acid, acid gastric vapours or gastric and/or duodenal juices besides the oesophagus, in the larynx, the oropharynx, the nasopharynx and the extraoesophageal areas, is defined as laryngopharyngeal disorder or Laryngopharyngeal Reflux Disease (LPRD) or pharyngolaryngeal reflux (abbreviated in PRL) or laryngopharyngeal reflux or extraoesophageal reflux.

Even though the "laryngopharyngeal reflux disorder" (abbreviated in LPRD) was initially considered as an extension of the gastroesophageal reflux disorder, in recent times it has been considered as a disorder or disease on its own, in particular in subjects at paediatric age (from birth to the beginning puberty, generally between 12 and 14 years) in that it is capable of locally determining pathological forms as a consequence.

In the context of the present invention, the upper respiratory airways, the eye bulb (or the eye), the periocular region, the nasolacrimal duct and the ear canal are referred to as extraoesophageal areas.

In the context of the present invention, the nasal cavity, the paranasal sinus, the oral cavity, the pharynx, the epiglottis and the larynx are referred to as upper respiratory airways.

In the context of the present invention, the region between the eye or regarding the eye contour, such as for example the conjunctiva and the lacrimal apparatus (comprising the nasolacrimal ducts), are referred to as the periocular region.

The conjunctiva is a mucosa membrane, which covers the eyeball and the inner part of the eyelids.

The lacrimal apparatus is the set of secretory organs of the lacrimal film, which includes the lacrimal gland, and of the apparatus that allows the outflow thereof. The apparatus that allows the outflow includes the lacrimal ways, consisting of: lacrimal points, lacrimal sac and nasolacrimal ducts (or lacrimal ducts or lacrimal canals or nasolacrimal ducts).

In the context of the present invention, the ear canal comprises the Eustachian tube which connects the middle ear to the pharynx, and the middle ear.

In other words, when the gastric acid flows back from the stomach, irritative conditions that can involve, for example, the larynx, the pharynx, the epiglottis, the oral cavity, the nasal cavity, the paranasal sinus, the ear canal, (e.g. the Eustachian tube and the middle ear), the eyeball (or the eye) and the periocular region (e.g. the conjunctiva and the nasolacrimal ducts) may occur at the extraoesophageal areas level.

In the context of the present invention, the expressions "laryngopharyngeal disorder", "laryngopharyngeal reflux disorder" (LPRD), "laryngopharyngeal reflux", "pharyngolaryngeal reflux" (LPR), "extraoesophageal reflux" or "backflow of the gastric content or acid gastric vapours from the stomach into an extraoesophageal area" will be used interchangeably to indicate what has been defined above.

Thus, an object of the present invention is to provide mixtures or formulations or preparations or compositions for use for the preventive and/or curative treatment of extraoesophageal disorders or symptoms caused or triggered by gastroesophageal reflux disease (GERD); said disorders being related to or arising from or connected to the extraoesophageal reflux or laryngopharyngeal reflux.

Another object of the present invention is to provide a composition for use in said preventive and/or curative treatment that is effective, stable, easy to take/apply and that, once applied, is well-tolerated by the majority of subjects and basically free of adverse effects.

These and other objects which will be clear from the detailed description that follows, are attained by the mixture and composition of the present invention due to the technical characteristics claimed in the attached claims.

Forming an object of the present is a mixture (hereinafter referred to as mixture of the present invention) in solid form comprising or, alternatively, consisting of:
 (a) an alginic acid or a salt thereof regarding an alkaline metal or of an alkaline earth metal;
 (b) a bicarbonate salt of an alkaline metal or alkaline earth and/or a carbonate salt of an alkaline metal or alkaline earth;
 (c) a simethicone and/or dimethicone.

Preferably, the mixture of the present invention comprises or, alternatively, consists of (a), (b) and (c), as defined in the context of the present invention, with the condition that said mixture does not comprise a histamine H2 receptor antagonist (H2 antagonist), such as for example ranitidine, famotidine or cimetidine.

Preferably, in said mixture, in association with (b) and (c), said alginic acid (a) is preferably an alginic acid having an average molecular weight comprised between about 50 KDaltons and about 1000 KDaltons; more preferably, in said mixture said alginic acid (a) has an average molecular weight comprised between about 100 KDaltons and about 800 KDaltons. Said mixture contains said alginic acid, preferably an alginic acid (a) having an average molecular weight comprised between about 200 KDaltons and about 600 KDaltons; more preferably, in said mixture said alginic acid (a) has an average molecular weight comprised between about 300 KDaltons and about 400 KDaltons.

The mixture preferably contains said alginic acid (a) preferably having an average molecular weight of about 240,000 Daltons (240 KDaltons—atomic mass unit) and obtained from marine algae.

The alginic acid (a) used in the mixture is preferably in form of an alginate salt; more preferably, in said mixture said alginate salt is selected from among the group comprising or, alternatively, consisting of sodium alginate, potassium alginate, calcium alginate or magnesium alginate.

Alginic acid is a polysaccharide consisting of two types of uronic acid: Mannuronic acid unit (M) and Guluronic acid unit (G), which form two types of polymeric segment blocks: M blocks with M-M bonds only; G blocks with G-G bonds only; M&G random blocks with M-G random bonds.

Examples of alginic acid and alginates (a) used in the present invention together with (b) and (c) are represented by:

Alginic acid EP (CAS n. °9005-32-7) in form of a straw yellow powder with an average grain size of about 80 mesh, a viscosity less than or equal to 50 cPs, an acidity index greater than or equal to 230, carboxylic groups of about 9-25, a pH of about 2-3.5.

Calcium alginate, CAS n. °90005-35-0, with general formula $(C_6H_7Ca_{1/2}O6)n$; structural units 195.16 (theoretical), 219 (average) and macromolecules: 10,000-600,000 (typical average).

Magnesium alginate (KIMICA ALGIN MAG-60, CAS n. °37251-44-8) (composition: Guluronic acid of about 65-75% and Mannuronic acid of about 25-35% and a magnesium content of about 5.4-6.6) with a pH value of about 6-9,5, a viscosity (CPS) (LV, 12 RPM) 7.5% natural basic solution, 25° C. of about 1,000-1,800.

Potassium alginate, CAS n. °90005-36-1, with general formula $(C_6H_7KO_6)n$; structural units 214.22 (theoretical), 238 (average) and macromolecules: 10,000-600,000 (typical average).

Satialgine™ S 110 (composition: sodium alginate E401 and saccharose) with a viscosity of about 550-750 mPa s (1% sol.) and pH of about 6-8.5 (1% sol.).

Sodium alginate, CAS n. °90005-38-3, with general formula $(C_6H_7NaO_6)n$; structural units 198,11 (theoretical), 222 (average) and macromolecules: 10,000-600,000 (typical average).

In a preferred embodiment, in said mixture, in association with (b) and (c), the alginic acid (a) present is preferably alginic acid CAS no. 9005-32-7 or magnesium alginate CAS n. °37251-44-8.

The mixture of the present invention comprises [in association with said alginic acid (a) and simethicone/dimethicone (c)] (b): a bicarbonate salt of an alkaline metal or alkaline earth and/or a carbonate salt of an alkaline metal or alkaline earth.

The mixture of the present invention comprises a bicarbonate salt of an alkaline metal or of an alkaline earth metal (b) selected from among the group comprising or, alternatively, consisting of sodium bicarbonate, potassium bicarbonate, magnesium carbonate and calcium carbonate, and/or a carbonate salt of an alkaline metal or of an alkaline earth metal (b) selected from among the group comprising or, alternatively, consisting of sodium carbonate, potassium carbonate, magnesium carbonate and calcium carbonate.

An example of potassium bicarbonate (b) is (E501 ii) with general formula $HKCO_3$, molecular weight 100,12 and EINECS n. °298-14-6 and a Bulk density of about 0.99-1.12 g/cm$^3$ and a Tapped density of about 1.14-1.25 g/cm$^3$.

The mixture of the present invention comprises [in association with said alginic acid (a) and said bicarbonate and/or said carbonate salt (b)] (c): a simethicone and/or dimethicone.

The mixture of the present invention comprises a simethicone compound, or a dimethicone compound, or a simethicone compound and a dimethicone compound together.

Examples of simeticone or simethicone (c) to be used in association with (a) and (b) are represented by:

Simethicone ANTIFOAM 30 MG in form of water-soluble simethicone (aqueous emulsion) with an antifoam activity of 15 seconds max. and an active content comprised between 29% and 32% by weight and a density of about 1 g/cm$^3$.

BC Simethicone Antifoam C100F, this compound consists of a fluid polydimethylsiloxane (PDMS) and a silica aerogel. The silica aerogel activates the antifoam properties of the fluid silicon. This compound has a specific gravity at 25° C. of about 0.1; a viscosity at 25° C. of about 3000 cP; an efficiency less than 15 seconds; a composition of PDMS of about 92.5-97.5% and silica of about 4-7%.

Simethicone SILFAR® SE4 in form of an emulsion with a solid content of about 31-34% by weight; an active gradient ("Simethicone", USP) of about 30% by weight, a density at 25° C. of about 1 g/ml, a viscosity at 25° C. of about 1500-5000 mPas, a pH at 25° C. of about 3-5.

Preferably, said simethicone is the simethicone CAS no. 8050-81-5; or even one belonging to the following classes of simethicone: Simethicone 100, Simethicone Emulsion 30%, Simethicone Emulsion, Antifoam C 100 (C100F), Antifoam 30 PD, Antifoam PD30 S, Antifoam 30 MG.

Examples of dimeticone or dimethicone are represented by:

Dimethicone ACESIL 350, CAS n. °63148-62-9, in liquid form with a kinematic viscosity at 25° C. of about 332.5-367.5 mm2/s, a density at 25° C. of about 0.9660-0.9720 g/ml, a refractive index at 25° C. of about 1.4025-1.4045, chemical name polydimethylsiloxane.

Dimethicone ABIL®350, CAS n. °63148-62-9, in liquid form with a refractive index of about 1.4030-1.4050, a density at 25° C. of about 0.95-0.97 g/ml and a viscosity at 25° C. of about 332-368 mm2/s.

PEG-14 Simethicone ABIL® B 8843 (components: PEG-14 Simethicone 95% by weight and propylene glycol 5% in peso), CAS n. °68937-54-2, in liquid form with a refractive index of about 1.4500-1.4600, a density at 25° C. of about 1.063-1.077 g/ml and a viscosity at 25° C. of about 300-600 mPas;

Dimethicone ABIL® WAX 2434 (component: Stearoxy Dimethicone 100%), CAS n. °68554-53-0, with a refractive index of about 1.4210-1.4270, a density at 50° C. of about 0.8600-0.9000 g/ml and a recrystallisation of about 20-30° C.

Preferred examples of dimethicone are: Cetyl dimethicone, Stearyl dimethicone, Stearoxy dimethicone, Behenoxy dimethicone and all polymers belonging to the group of dimethicone copolyols such as for example: Dimethicone PEG-8 Adipate, Dimethicone PEG-8 Benzoato, Dimethicone PEG-7 Phosphate, Dimethicone PEG-10 Phosphate, Dimethicone PEG/PPG-20/23 Benzoate, Dimethicone PEG/PG-7 Dimethicone, PEG-10 Dimethicone, PEG-9 Dimethicone, PEG-10 Dimethicone, PEG-12 Dimethicone, PEG-3 Dimethicone, PEG-7 Dimethicone, PEG-14 Dimethicone, PEG/PPG-8/14 Dimethicone, PEG/PPG-3/10 Dimethicone, PEG/PPG-4/12 Dimethicone, PEG/PPG-6/11 Dimethicone, PEG/PPG-4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/PPG-20/6 dimethicone, PEG/PPG-20/15 dimethicone, PEG/PPG-20/20 dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone and PEG/PPG-27/27 dimethicone.

In a preferred embodiment, in said mixture, in association with (a) and (b), the simethicone (c) present is preferably the simethicone CAS no. 8050-81-5.

Advantageously, the mixture of the present invention comprises or, alternatively, consists of:
(a) a magnesium alginate;
(b) a potassium bicarbonate;
(c) a simethicone and/or dimethicone.

In the mixture of the present invention it is observed that:
(a) said alginic acid, or a relative salt thereof of an alkaline metal or of an alkaline earth metal, is present in said mixture at an amount by weight comprised between 20% and 70% with respect to the total weight of the mixture comprising or, alternatively, consisting of (a), (b) and (c); preferably it is present at an amount by weight comprised between 40% and 60%;
(b) said bicarbonate salt of an alkaline metal or of an alkaline earth metal and/or said carbonate salt of an alkaline metal or of an alkaline earth metal, is present in said mixture at an amount by weight comprised between 5% and 30% with respect to the total weight of the mixture comprising or, alternatively, consisting of (a), (b) and (c); preferably it is present at an amount by weight comprised between 10% and 25%;
(c) said simethicone and/or dimethicone, is present in said mixture at an amount by weight comprised between 5% and 30% with respect to the total weight of the mixture comprising or, alternatively, consisting of (a), (b) and (c); preferably it is present at an amount by weight comprised between 10% and 25%.

The mixture of the present invention is in form of powder, granules, chips, capsules, tablets, bars, comfits or other solid forms known to a man skilled in the art.

A mixture, as described above (mixture of the present invention), for use in the treatment of symptoms, disorders and effects caused or triggered by the gastroesophageal triggered by gastroesophageal reflux, forms an object of the present invention.

A mixture, as described above (mixture of the present invention), for use in the treatment of extraoesophageal symptoms, disorders or effects caused or triggered by the pharyngolaryngeal reflux and/or backflow of the gastric content or of the acid gastric vapours from the stomach into an extraoesophageal area (as defined in the context of the present invention) such as the pharynx and the upper respiratory airways comprising the ear canal and the nasolacrimal duct, forms an object of the present invention.

Preferably said mixture is for use in the treatment of patients suffering from the gastroesophageal reflux disease GERD. Alternatively, the mixture of the invention is for use in the treatment of extraoesophageal symptoms, disorders or effects caused or triggered by the pharyngolaryngeal reflux and/or the backflow of the gastric content or acid gastric vapours from the stomach into an extraoesophageal area in patients not suffering from GERD or non-diagnosed suffering from GERD.

Advantageously, said mixture is for use in the protection of the mucosae and for reducing the damage caused thereto. Said mucosae are mucosae of a gastroesophageal area or of an extraoesophageal area. Preferably said mucosae are of an extraoesophageal area, such as the mucosae or the tissues of the inner walls of the upper respiratory airways (e.g. the larynx, the pharynx, the epiglottis, the oral cavity, the nasal cavity, the paranasal sinus), the eye ball (or the eye), periocular region (e.g. the conjunctiva and nasolacrimal ducts) and the ear canal (e.g. the Eustachian tubes and the middle ear), as defined in the context of the present invention.

A composition (hereinafter referred to as composition of the invention) comprises a mixture (mixture of the present invention comprising or, alternatively, consisting of (a), (b) and (c)), as described above, and optionally, at least one food grade or pharmaceutical excipient or additive, forms an object of the present invention.

Preferably, the composition of the present invention doers not comprise a histamine H2 receptor antagonist (H2 antagonist), such as for example ranitidine, famotidine or cimetidine.

Said food grade or pharmaceutical excipient or additive is advantageously selected from among the group comprising sorbitol, mannitol, calcium phosphate dibasic anhydrous, flavour, silicon dioxide, corn starch, vegetable magnesium stearate, sucralose, cellulose and derivatives and microcrystalline cellulose.

The alginic acid and the alginates (a) are present together a (b) and (c) at an amount by weight comprised between 1% and 30%, preferably between 10% and 20% by weight, with respect to the final weight of the composition; the bicarbonate salt (b) is present at an amount by weight comprised between 0.1% and 15%, preferably between 1% and 8% by weight, with respect to the final weight of the composition, while the simethicone or dimethicone (c) is present at an amount by weight comprised between 0.05% and 15%, preferably between 0.5% and 5% by weight, with respect to the final weight of the composition.

The composition of the present invention comprises the mixture of the present invention at a ratio by weight comprised between 1:10 [mixture: composition] a 1:2 [mixture: composition]; preferably at a ratio by weight of about 1:4 [mixture: composition] or at a ratio by weight of about 1:3 [mixture: composition].

The composition of the present invention is in solid form in form of powder, granules, chips, capsules, tablets, bars, comfits or other solid form known to a man skilled in the art.

In a preferred embodiment, the composition has the following formula for 100 g:
Sorbitol: 40 g
Magnesium alginate: 17 g
Mannitol: 14 g
Calcium phosphate dibasic anhydrous: 5 g
Potassium bicarbonate: 5 g
Flavour: 5 g
Silicon dioxide: 4 g
Corn starch: 4.4 g
Simethicone: 3.5 g
Vegetable magnesium stearate 2 g
Sucralose: 0.1 g A composition (composition of the invention), as described above, for use in the treatment of symptoms, disorders or effects caused or triggered by gastroesophageal reflux, forms an object of the present invention.

A composition (composition of the invention), as described above, for use in the treatment of extraoesophageal symptoms, disorders or effects caused or triggered by the pharyngolaryngeal reflux and/or backflow of the gastric content or of the acid gastric vapours from the stomach into an extraoesophageal area (as defined in the context of the present invention) such as the pharynx and the upper respiratory airways comprising the ear canal and the nasolacrimal duct, forms an object of the present invention; preferably said mixture is for use in the treatment of patients suffering from the gastroesophageal reflux disease GERD.

Preferably said composition is for use in the treatment of patients suffering from the gastroesophageal reflux disease GERD. Alternatively, the composition of the invention is for use in the treatment of extraoesophageal symptoms, disorders or effects caused or triggered by the pharyngolaryngeal reflux and/or the backflow of the gastric content or acid gastric vapours from the stomach into an extraoesophageal area in patients not suffering from GERD or non-diagnosed suffering from GERD.

Advantageously, said composition is for use in the protection of the mucosae and for reducing the damage caused thereto. Said mucosae are mucosae of a gastroesophageal area or an extraoesophageal area. Preferably are of an extraoesophageal area, as defined in the context of the present invention. Furthermore, a preventive and/or curative method for the treatment of symptoms, disorders or effects caused or triggered by gastroesophageal reflux, or alternatively, by the extraoesophageal reflux forms an object of the present description, wherein said treatment method comprises the administration of the mixture or composition of the invention in solid form, as defined above, to a needy subject orally.

Lastly, the non-therapeutic use of the mixture or composition of the invention in solid form as defined above, for the non-therapeutic treatment of an altered physiological state arising from or relating to the gastroesophageal reflux, or alternatively, to the gastroesophageal reflux forms an object of the present description, wherein said non-therapeutic use comprises the administration of the mixture or composition of the invention to a needy subject orally.

Unless specified otherwise, the indication that a composition "comprises" one or more components means that other components besides the one, or the ones, indicated specifically, are present even though not necessarily indicated, meaning that the composition can also exclusively contain such components, and the indication that a composition "consists" of determined components means that the presence of other composition is excluded.

In the present invention, the expression "treatment" of a disease or disorder is used to indicate the therapy aimed at restoring a subject's health conditions, maintaining the current conditions and/or preventing the deterioration of said health conditions.

In the present invention, the expression "prevention" of a disease or disorder is used to indicate a therapy aimed at hindering the occurrence of such disease or disorder in a subject, including but not exclusively complication or effect of a pre-existing disease or disorder.

Unless indicated otherwise, in the present invention the percentages and amounts of a component in a mixture shall be deemed to refer to the weight of such component with respect to the total weight of the mixture.

Unless indicated otherwise, in the present invention, as regards the value intervals of numerical values for a given characteristic, the indication "from X to Y" comprises the extremities, i.e. X and Y, as well as all possible intermediate numerical values.

The composition according to the present invention can be for use in human subjects or for veterinarian use, by way of non-limiting example, in pets such as dogs or cats, or in other mammals. Preferably, the composition according to the present invention is for use in humans.

The composition of the present invention applies to use for the treatment of symptoms, disorders, diseases or effects caused or triggered by the backflow of the gastric content for example pepsin or acid gastric vapours or gastric and duodenal juices from the stomach into an extraoesophageal area, both in subjects suffering from GERD and in subjects not suffering from GERD.

The expression "medical device" in the context of the present invention is used according to the meaning laid down by the Italian Legislative Decree n °46, dated 24 Feb. 1997, corresponding to the definition provided by the World Health Organisation and available at http://www.who.int/medical_devices/full_deffinition/en/, i.e. it indicates a substance or another product, used alone or in combination, designated by the manufacturer to be used in humans for diagnosis, prevention, control, therapy or disease attenuation purposes, the product not exercising the main action, in or on the human body, for which it is designated, neither with pharmacological or immunology means nor by means of a metabolic process but the function thereof can be assisted by such means.

The composition (C) according to the present invention can be advantageously also used for the curative and/or preventive treatment of the diseases relating to gastroesophageal reflux disease (GERD), such as Barrett's oesophagus, adenocarcinoma of the distal tract of the oesophagus and oesophagitis, in GERD-related disorders such as dysphagia and odynophagia, both in subjects affected by or suffering from GERD and in subjects not affected by or not suffering from GERD, preferably in subjects suffering from gastroesophageal reflux disease GERD.

It should be observed that the use of (a) alginic acid, or a salt thereof; (b) a bicarbonate salt and/or a carbonate salt with an alkaline metal or alkaline earth; and (c) a simethicone or a dimethicone in the treatment of the symptoms and the diseases caused by the gastroesophageal reflux in an extraoesophageal area, both when (a), (b) and (c) are administered simultaneously, i.e. in mixture in the same composition, and when (a), (b) and (c) are administered to a subject, in any order and even in combination between two active ingredients only, in a close sequence over time in two or three separate compositions.

It was discovered that through the composition according to the invention it is possible to obtain a synergic effect of the components (a), (b) and (c) for the improvement and prevention of disorders and symptoms directly or indirectly caused or triggered by the gastroesophageal reflux and/or laryngopharyngeal reflux and/or generally the backflow of the gastric content or the acid gastric vapours from the stomach, wherein said disorders or symptoms are present in an extraoesophageal area, preferably in patients suffering from GERD.

In a preferred embodiment, the composition according to the present invention is for use as a coadjuvant for re-epithelisation processes of the gastric and/or oesophageal mucosa.

In an embodiment, the composition according to the present invention is in form of a solid preparation, such as for example, powder, capsule or tablet.

By way of non-limiting example, the excipients that can be included in the composition according to the present invention comprise preservatives, antioxidants, stabilisers, thickeners, rheology modifiers, biocides, colour additives, pH buffers and the like.

Both the composition and mixture subject of the present invention are prepared using techniques, methods and equipment known to a man skilled in the art.

Embodiments (FRn) of the present invention are indicated below:

FR1. A mixture in solid form comprising or, alternatively, consisting of:
(a) an alginic acid or a salt thereof regarding an alkaline metal or of an alkaline earth metal;
(b) a bicarbonate salt of an alkaline metal or alkaline earth and/or a carbonate salt of an alkaline metal or alkaline earth;
(c) a simethicone and/or dimethicone.

FR2. The mixture according to FR1, wherein said alginic acid is an alginic acid having an average molecular weight comprised between about 50 KDaltons and about 1000 KDaltons; more preferably said alginic acid has an average molecular weight comprised between about 100 KDaltons and about 800 KDaltons.

FR3. The mixture according to FR1 or FR2, wherein said alginic acid is preferably an alginic acid having an average molecular weight comprised between about 200 KDaltons and about 600 KDaltons; more preferably said alginic acid has an average molecular weight comprised between about 300 KDaltons and about 400 KDaltons.

FR4. The mixture according to FR1-FR3, wherein said alginic acid preferably has an average molecular weight of about 240,000 Daltons (240 KDaltons—atomic mass unit) and it is obtained from marine algae.

FR5. The mixture according to FR1-FR4, wherein said alginic acid is preferably in form of an alginate salt; more preferably said alginate salt is selected from among the group comprising or, alternatively, consisting of sodium alginate, potassium alginate, calcium alginate or magnesium alginate.

FR6. The mixture according to FR1-FR5, wherein said bicarbonate salt of an alkaline metal or of an alkaline earth metal is selected from among the group comprising or, alternatively, consisting of sodium bicarbonate, potassium bicarbonate, magnesium bicarbonate and calcium bicarbonate, and said carbonate salt of an alkaline metal or of an alkaline earth metal is selected from among the group comprising or, alternatively, consisting of sodium carbonate, potassium carbonate, magnesium carbonate and calcium carbonate.

FR7. The mixture according to FR1-FR6, wherein said simeticone or simethicone is selected from among the group comprising simethicone 100, simethicone emulsion 30%, simethicone emulsion, Antifoam C100, Antifoam 30PD, Antifoam PD30, Antifoam 30 MG.

FR8. The mixture according to FR1-FR7, wherein said dimethicone is selected from among the group comprising or, alternatively, consisting of: Cetyl dimethicone, Stearyl dimethicone, Stearoxy dimethicone, Behenoxy dimethicone and all polymers belonging to the group of dimethicone copolyols.

FR9. The mixture according to FR8, wherein said polymers belonging to the group of dimethicone copolyols are selected from among the group comprising or, alternatively, consisting of: Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PG-7 Dimethicone, PEG-10 Dimethicone, PEG-9 Dimethicone, PEG-10 Dimethicone, PEG-12 Dimethicone, PEG-3 Dimethicone, PEG-7 Dimethicone, PEG-14 Dimethicone, PEG/PPG-8/14 Dimethicone, PEG/PPG-3/10 Dimethicone, PEG/PPG-4/12 Dimethicone, PEG/PPG-6/11 Dimethicone, PEG/PPG-4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/PPG-20/6 dimethicone, PEG/PPG-20/15 dimethicone, PEG/PPG-20/20 dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone and PEG/PPG-27/27 dimethicone.

FR10. The mixture according to FR1-FR9, wherein said mixture comprises or, alternatively, consists of:
(a) a magnesium alginate;
(b) a potassium bicarbonate;
(c) a simethicone and/or dimethicone.

FR11. The mixture according to FR1-FR10, wherein:
(a) said alginic acid, or a relative salt thereof of an alkaline metal or of an alkaline earth metal, is present in said mixture at an amount by weight comprised between 20% and 70%, preferably between 40% and 60%;
(b) said bicarbonate salt of an alkaline metal or of an alkaline earth metal and/or said carbonate salt of an alkaline metal or of an alkaline earth metal, is present in said mixture at an amount by weight comprised between 5% and 30%; preferably it is present at an amount by weight comprised between 10% and 25%;
(c) said simethicone and/or dimethicone, is present in said mixture at an amount by weight comprised between 5% and 30%; preferably it is present at an amount by weight comprised between 10% and 25%.

FR12. The mixture according to FR1-FR11, wherein said composition is in solid form in form of powder, granules, chips, capsules, tablets, bars or comfits.

FR13. The mixture according to FR1-FR12, wherein said mixture is for use in the treatment of symptoms, disorders or effects caused or triggered by gastroesophageal reflux.

FR14. The mixture according to FR1-FR12, wherein said mixture is for use in the treatment of extraesophageal symptoms, disorders or effects caused or triggered by the pharyngolaryngeal reflux and/or backflow of the gastric content or of the acid gastric vapours from the stomach into an extraesophageal area such as the pharynx and the upper respiratory airways comprising the ear canal and the nasolacrimal duct; preferably said mixture is for use in the treatment of patients suffering from gastroesophageal reflux disease GERD.

FR15. The mixture according to FR1-FR12, wherein said mixture is for use in the protection of the mucosae and for reducing the damage caused thereto.

FR16. A composition comprising a mixture according to any one of FR1-FR12 and, optionally, at least one food grade or pharmaceutical excipient or additive.

The invention claimed is:
1. A method of treatment, comprising:
orally administering a composition to a patient having extraoesophageal symptoms caused by laryngopharyngeal reflux (LPR), wherein the composition is in solid form and comprises:
(a) an alginic acid or a relative salt thereof of an alkaline metal or of an alkaline earth metal;
(b) a bicarbonate salt of an alkaline metal or alkaline earth and/or a carbonate salt of an alkaline metal or alkaline earth; and
(c) a simethicone and/or dimethicone, and
wherein said composition does not comprise a H2 receptor antagonist.

2. The method of claim 1, wherein said alginic acid is an alginic acid having an average molecular weight comprised between about 50 KDaltons and about 1000 KDaltons.

3. The method of claim 1, wherein said alginic acid is an alginic acid having an average molecular weight comprised between about 200 KDaltons and about 600 KDaltons.

4. The method of claim 1, wherein said alginic acid has an average molecular weight of about 240,000 Daltons (240 KDaltons—atomic mass unit) and it is obtained from marine algae.

5. The method of claim 1, wherein said alginic acid is in form of an alginate salt.

6. The method of claim 1, wherein said bicarbonate salt of an alkaline metal or of an alkaline earth metal is selected from among the group consisting of sodium bicarbonate, potassium bicarbonate, magnesium bicarbonate and calcium bicarbonate, and said carbonate salt of an alkaline metal or of an alkaline earth metal is selected from among the group consisting of sodium carbonate, potassium carbonate, magnesium carbonate and calcium carbonate.

7. The method of claim 1, wherein said simethicone is selected from among the group consisting of: simethicone 100, simethicone emulsion 30%, simethicone emulsion, Antifoam C100, Antifoam 30PD, Antifoam PD30, Antifoam 30 MG.

8. The method of claim 1, wherein said dimethicone is selected from among the group consisting of: Cetyl dimethicone, Stearyl dimethicone, Stearoxy dimethicone, Behenoxy dimethicone and all polymers belonging to the group of Copolyol dimethicones.

9. The method of 8, wherein said polymers belonging to group of Copolyol dimethicones are selected from the group consisting of: Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PG-7 Dimethicone, PEG-10 Dimethicone, PEG-9 Dimethicone, PEG-10 Dimethicone, PEG-12 Dimethicone, PEG-3 Dimethicone, PEG-7 Dimethicone, PEG-14 Dimethicone, PEG/PPG-8/14 Dimethicone, PEG/PPG-3/10 Dimethicone, PEG/PPG-4/12 Dimethicone, PEG/PPG-6/11 Dimethicone, PEG/PPG-4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/PPG-20/6 dimethicone, PEG/PPG-20/15 dimethicone, PEG/PPG-20/20 dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone and PEG/PPG-27/27 dimethicone.

10. The method of claim 1, wherein said composition comprises:
    (a) a magnesium alginate;
    (b) potassium bicarbonate; and
    (c) a simethicone and/or dimethicone.

11. The method of claim 1, wherein:
    (a) said alginic acid, or a relative salt thereof of an alkaline metal or of an alkaline earth metal, is present in said mixture at an amount by weight comprised between 20% and 70% with respect to the total weight of the mixture;
    (b) said bicarbonate salt of an alkaline metal or of an alkaline earth metal and/or said carbonate salt of an alkaline metal or of an alkaline earth metal, is present in said mixture at an amount by weight comprised between 5% and 30% with respect to the total weight of the mixture;
    (c) said simethicone and/or dimethicone, is present in said mixture at an amount by weight comprised between 5% and 30% with respect to the total weight of the mixture.

12. The method of claim 1, wherein the patient has symptoms in the eye and/or in the periocular region.

13. The method of claim 1, wherein the patient is not diagnosed as suffering from GERD.

* * * * *